United States Patent [19]

Leiske

[11] Patent Number: 4,560,383

[45] Date of Patent: Dec. 24, 1985

[54] ANTERIOR CHAMBER INTRAOCULAR LENS

[76] Inventor: Larry G. Leiske, 1500 S. Central, Suite 221, Glendale, Calif. 91204

[21] Appl. No.: 545,829

[22] Filed: Oct. 27, 1983

[51] Int. Cl.$^4$ ............................ A61F 1/16; A61F 1/24
[52] U.S. Cl. ........................................................ 3/13
[58] Field of Search ............................................ 3/13, 1

[56] References Cited

U.S. PATENT DOCUMENTS 4,377,873  3/1983  Reichert, Jr. .............................. 3/13

OTHER PUBLICATIONS

The Leiske Physioflex Style 10 Anterior Chamber Lens, advertisement by Surgidev Corp., Santa Barbara, Calif., 1981.
Intraocular Lenses from McGhan/3M, Anterior Chamber Liteflex Style 70 Intraocular Lens, advertisement by McGhan Medical/3M, 3M Center, St. Paul, MN 55144, 2 pages.

Primary Examiner—Ronald L. Frinks
Attorney, Agent, or Firm—Hugh D. Jaeger

[57] ABSTRACT

Anterior chamber lens including a lens optic and two flexible opposing loops secured into a side edge of the optic. Each loop is substantially U-shaped and each opposing arm of the loop includes a slight ramp providing a vault for the lens with respect to each base member of each loop. The lens and loop are constructed from a single monomer or monofilament material, polymethylmethacrylate (PMMA), providing for stability, low mass, and flexibility. The loops are flexible in three degrees of freedom, particularly end-to-end. The lens can be utilized in both primary and secondary implantations with either intracapsular or extracapsular cataract extractions. Each lens end base member is kicked up at an angle with a flat portion disposed between the ramped portion and the base member. The base member can also be curved inwardly towards the lens. The kicked up ends eliminates and reduces ovaling of the pupil in addition to preventing the lens from bowing forward. The kicked up end of the base member can be in a range of 0.0–0.25 mm while 0.12 mm is the preferred range.

6 Claims, 9 Drawing Figures

ANTERIOR CHAMBER INTRAOCULAR LENS

CROSS REFERENCES TO CO-PENDING APPLICATIONS

This application relates to Ser. No. 315,714 filed on Oct. 29, 1981.

BACKGROUND OF THE INVENTION

1. Field of the Invention

The present invention relates to an intraocular lens and, more importantly, pertains to an anterior chamber lens for primary or secondary implantation.

2. Description of the Prior Art

Prior art anterior chamber lenses suffered from numerous deficiencies. Some prior art lenses were constructed from types of materials that caused significant implant material reactions in the eye. Other prior art lenses required large amounts of material in construction of the implant. Also, the prior art lenses did not always have smooth surfaces, which resulted in postoperative reaction.

Most importantly, the prior art lenses failed to provide flexibility in the supporting structure, thereby leading to post-operative tenderness.

Other types of prior art lenses were manufactured from two types of material where the lens optics were manufactured from a first type of material, and the supporting structure which takes many geometrical variations was manufactured from a second type of material. This type of lens led to postoperative reactions. In some instances, the materials were found to dissolve in the body after implant.

Some prior art lenses were manufactured by machining, hot pressing, or pantographing, yielding a less than flexible lens. Also, the edges of the lens were not smooth.

Finally, some types of lenses were lathe cut from types of material which resulted in uneven surfaces and edges, causing postoperative reactions.

The present invention overcomes the disadvantages of the prior art by providing a smooth, flexible, one-material anterior chamber lens.

SUMMARY OF THE INVENTION

The general purpose of the present invention is an anterior chamber lens for any type of cataract extraction, and is also excellent for secondary or exchange implantation. The lens is flexible and soft to the human touch.

According to one embodiment of the present invention, there is provided an anterior chamber lens including an optic having a planar surface, a slightly rounded edge, and a convex surface, two opposing U-shaped flexible loops of the same material as the lens optic and having a slightly greater length in each arm than at a base, the opposing arms of each loop substantially parallel and including a ramp of a slight angle, each end of each loop frictionally and mechanically engaged into each hole positioned into the side of the lens, the base which is angled and kicked up and which can be curved inwardly, whereby the lens is utilized both in primary and secondary implantations either with intracapsular or extracapsular cataract extractions and the lens support is flexible in three dimensions and to the touch. The optic and loops of the lens are manufactured from polymethylmethacrylate (PMMA) and includes less optic supporting area available for iris touch than the prior art anterior chamber lenses.

One significant aspect and feature of the anterior chamber lens of the present invention is a lens having smooth surfaces, thus eliminating post-operative reaction.

Another significant aspect and feature of the anterior chamber intraocular lens of the present invention is a lens constructed and made entirely of polymethylmethacrylate, providing for flexibility with adequate strength and rigidity. The PMMA is pure material, a single low monomer material which has a long-proved history of intraocular use. During manufacturing, the material provides that internal stress forces in the loops can be eliminated, thereby preventing warpage. PMMA was originally used in Spitfire canopies during World War II.

A further significant aspect and feature of the anterior chamber intraocular lens of the present invention is a lens of PMMA material which is of low mass by weight and surface area.

One of the most significant aspects and features of the present invention is the flexibility of the loops of the lens. The loops are flexible in all directions including side-to-side, end-to-end, up-and-down, and in three dimensions. The flexible loops are twistable as well as compressible. The loops show a finite ease of flexibility. The loops exhibit physiologic flex. As the eye blinks, the loops flex. If the eye is compressed, the loops flex. On examination of the eye by a surgeon or examining physician, the loops exhibit flex. The flexibility of the loops is such that the lens is inserted by a surgeon in one motion through a limbal as there is no torquing about the axis of the lens. The loops provide three-dimensional flexibility about the lens optic.

Having thus described the invention, it is a principal object hereof to provide an anterior chamber lens, the lens denoted in the medical profession as the "Leiske Physioflex Style 10 Anterior Chamber Intraocular Lens" with a "kicked up" base.

It is a principal object hereof to provide an anterior chamber lens which is lightweight, flexible, and manufactured of one material. The optic and loops can be an integral member.

Objects of the present invention include an anterior chamber lens which has no significant post-operative tenderness. There is also a need for only a single iridectomy because of the design; a single peripheral iridectomy inside the loop is adequate. The anterior chamber lens also provides for easier insertion in that proper technique provides for the insertion of both angles of the superior loop in one motion. There is also excellent dilability of the pupil in that there is no interference with pupil dilation thereby making retinal inspection and surgical procedures easier. The lens is excellent for primary or secondary implantation, and provides for either an intracapsular or extracapsular cataract extraction.

An additional object of the present invention is a low-mass, low-weight lens made of one material, PMMA. The material provides a low mass in aqueous humor thereby reducing the possibility of reaction and internal stress due to eye movement or sudden movement. The material also provides extreme smoothness on all surfaces thereby eliminating chance of abrasion or irritation secondary to iris movement should contact occur. The PMMA provides a uniform material and longevity for least reaction. More importantly, though, the material provides for desirable flexibility but adequate rigidity assuring that there be no danger of endothelial touch. The lens is designed with adequate vault, providing for no significant contact with the iris.

Further objects of the present invention include an anterior chamber lens which provides implant considerations of importance to the surgeon as well as to the patient. Those considerations include greatly diminished post-operative global tenderness, less hyphema associated with accidental or diagnosed trauma such as scleral depression, optic supporting surface area available for iris touch substantially 84% less than with prior art lenses, no acutely angled feet to pass through iridectomy and inadvertently engage cillary body, less likelihood of Descemet's membrane stripping caused by catching acutely angled feet, greatly reduced possibility of segmental iris block, no large lens feet capable of occluding iridectomy or irridotomy, no torquing around axis of lens while inserting the superior loop, 6 mm lens optic to insure complete optical covering of the pupil, the lens nearly precluding possibility of uveitis, glaucoma or hyphema because of design and method manufacture, a lens with shape which diminishes iris tucking or iris tearing, and a lens which is less likely to engage vitreous humor because of lack of acutely angled feet. Finally, the PMMA lens does not activate complement. Additionally, the PMMA loops and optic provide smooth edges eliminating any finishing problems which existed in the prior art. The monofilament loops provide smoothness and no finishing is required.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF PREFERRED EMBODIMENTS

Figure 1:
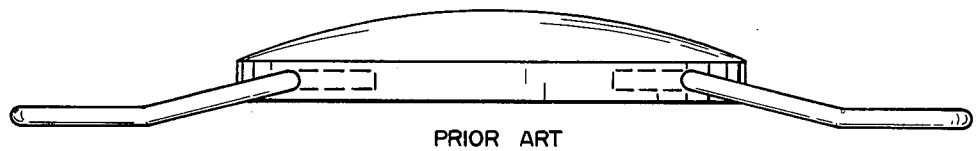
FIG. 1 illustrates a side view of a prior art lens.

FIG. 1 illustrates a side view of a prior art lens where the base is a flat portion. Particular notation is made of the vaulted distance between the planar surface of the lens and the lower edge of the members and which is preferably in a range of 0.4–0.6 mm, by way of example and for purposes of illustration only, and not to be construed as limiting of the present invention, and preferably 0.5 mm.

Figure 2:
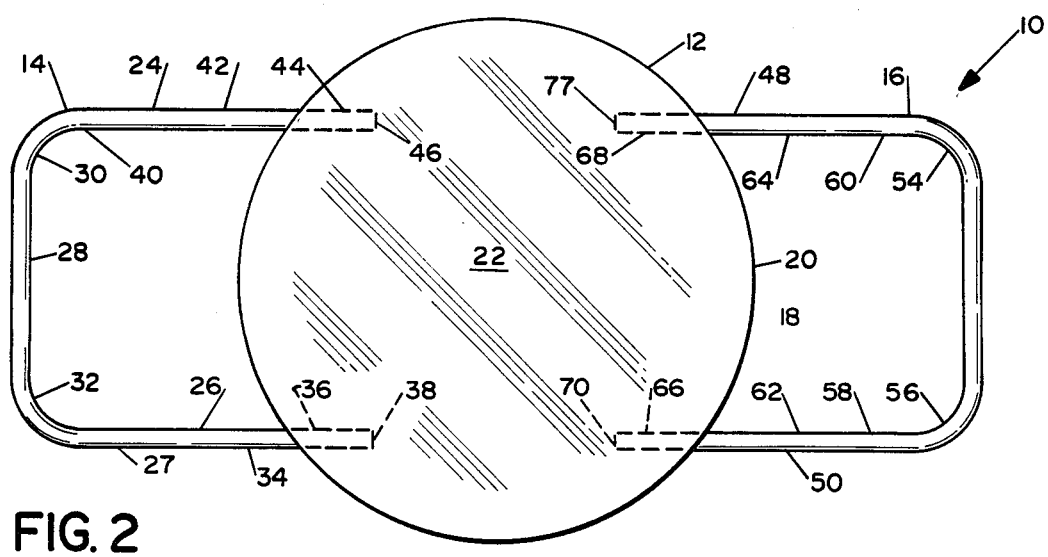
FIG. 2 illustrates a top view of an anterior chamber lens, the present invention.

FIG. 2, which illustrates a top view of an anterior chamber lens 10, the present invention, shows the lens optic 12, a first U-shaped flexible loop 14 and a scond U-shaped flexible loop 16 where both or the loops 14 and 16 are diametrically opposed to each other at opposite sides of the lens optic 12. The lens optic 12 includes a planar surface 18, a thin side edge of finite width 20, and a convex surface 22, as also illustrated in FIG. 2. The lens optic 12 and the loops 14 and 16 are manufactured of a material known as polymethylmethacrylate (PMMA) The diameter of the lens optic 12 is a range of 4–7 mm and can have varying dioptric powers substantially in the range of 9–30.

The lens 10 is provided with two PMMA loops 14 and 16. The first loop 14 is now described in detail with the second loop 16 being identical to loop 14.

Figure 3:
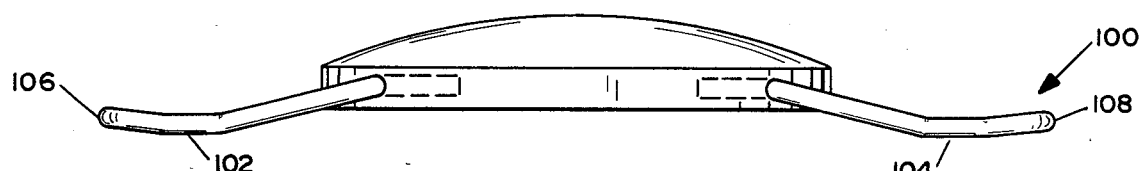
FIG. 3 illustrates a side view of the lens of FIG. 1 with a slightly kicked-up end.

The loop 14 is a substantially U-shaped member having two opposing arms 24 and 26 connected by a base 28, with rounded corners 30 and 32. The loops are substantially 0.25 mm in diameter in a range of 0.08–0.50 mm and are canted including a like ramp in each arm referenced in FIG. 3. The ramp of arm 26 is best illustrated in FIG. 3 where the ramp section 34 connects between a lower section 27 and an end section 36, sections 27 and 36 being in substantially the same parallel plane and connected by the ramp member 34. The end 36 mechanically and frictionally engages into a hole 38 in the edge 20 of the lens 10. Likewise, the opposing arm 24 is provided with a ramp 42 between lower section 40 and an end 44 which engages into a hole 46 in the lens 10 in a like manner. The holes 38 and 46 are provided and drilled into the side 20 of the lens 10. Accordingly, arms 24 and 26 are identical as illustrated in FIG. 1 and referenced in FIG. 3. The loop 14 has a preferred circular geometrical cross-section of a cylinder, but any other geometrical cross-section could be utilized such as an ovoid or ribbon.

Likewise, the loop 16 is provided with arms 48 and 50, and base member 52 where the arms 48 and 50 connect to the base member 52 by rounded corners 54 and 56. Each of the arms of the loop 16 includes a lower section 58 and 60, ramps 62 and 64, and ends 66 and 68 mechanically and frictionally engage into holes 70 and 72 as previously described. All ends are subsequently heat staked into the holes.

By way of example and for purposes of illustration only and not to be construed as limiting of the present invention, the distance between the arms of each of the loops 14 and 16 is preferably in a range of 2–10 mm. The distance between the arms 48 and 50 is likewise 2–10 mm. The diameter of the lens 10 is referenced between the opposing rounded corners such as 32 and 54, and the lens is manufactured from 10.5 mm to 14.0 mm with 12.5 mm being the most common implant size. Diametrical length of the lenses is manufactured in 0.5 mm increments from 10.5 to 14.0 mm, although the lenses can be manufactured to any increment as determined by a surgeon.

FIG. 3 illustrates a side view of a lens of the present invention with a slightly kicked-up base 100 including slightly planar base portions 102 and 104, and kicked-up base ends 106 and 108. The slightly planar sections 102 and 104 between the ramp and the base have a finite length and provides for least minimal surface contact with the iris. The degree of angle of the slightly kicked-up base is a height of 0.12 mm between the planar section and the end of the base accordingly by way of example and for purposes of illustration. All other elements correspond to elements of FIG. 2.

Figure 4:
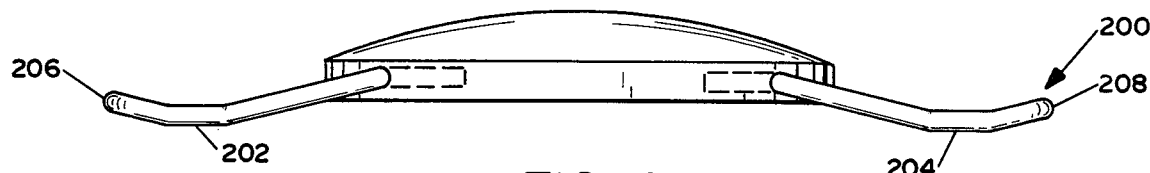
FIG. 4 illustrates a side view of the lens of FIG. 1 with a kicked-up end.

FIG. 4 illustrates a side view of the present invention with a kicked-up base 200 including slightly planar portions 202 and 204, and kicked-up base ends 206 and 208. The degree of angle of the slightly kickec-up base is a height of 0.25 mm between the planar section and the end of the base. All other elements correspond to elements of FIG. 2

Figure 5:
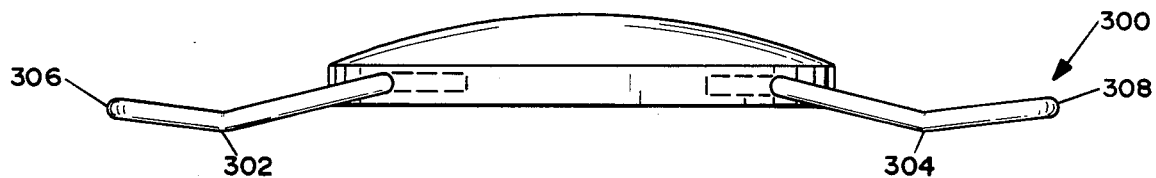
FIG. 5 illustrates a side view of the lens of FIG. 1 with a substantially kicked-up end.

FIG. 5 illustrates a side view of the invention including a substantially kicked-up base ends 300 including apexes 302 and 304, and kicked-up base end 306 and 308. The apexes do not include a planar portion, and disclose that the ramp at the apex goes into immediately kicked-up base portion 300. This provides for very minimal iris contact at the point of contact of the apex between the ramp and the kicked-up base end. All other elements correspond to elements of FIG. 2.

Figure 6:
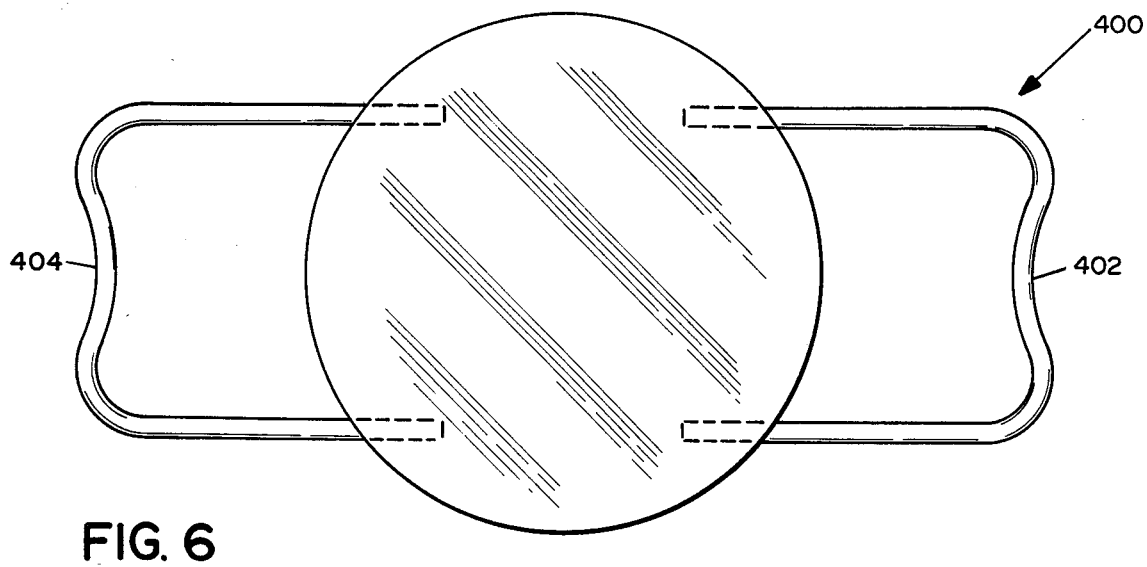
FIG. 6 illustrates a top view of an alternative embodiment of the lens of FIG. 1.

FIG. 6 illustrates a top view of an alternative embodiment of the present invention of an anterior chamber lens 400, which includes base members having a slightly inward curved end 402 and 404. All other elements and aspects of the lens is identical to that described in FIGS. 2–5.

Figure 7:
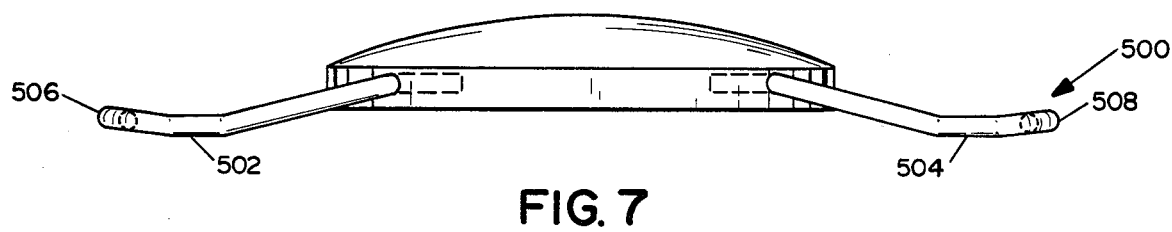
FIG. 7 illustrates a side view of a lens of FIG. 6 with a slightly kicked-up end.

FIG. 7 illustrates a side view of a lens 500 having slightly kicked-up base ends 506 and 508, similar to that of FIG. 3 and including the inward curved ends as illustrated in FIG. 6. This lens includes slightly planar sections 502 and 504.

Figure 8:
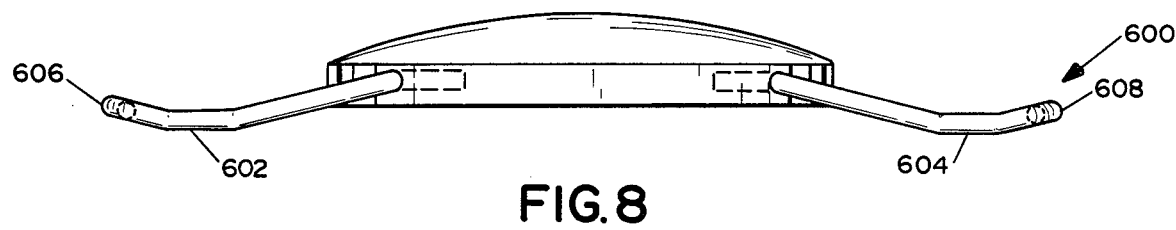
FIG. 8 illustrates a side view of the lens of FIG. 6 with a kicked-up end.

FIG. 8 illustrates a side view of a lens 600 having kicked-up base ends 606 and 608 included inward curved ends as illustrated in FIG. 6, and a slightly planar sections 602 and 604. The difference between FIG. 7 and FIG. 8 is the degree of height of the kicked-up base end, which in FIG. 7 is 0.12 mm and in FIG. 8 is 0.25 mm by way of example and for purposes of illustration, and not to be construed as limiting of the present invention.

Figure 9:
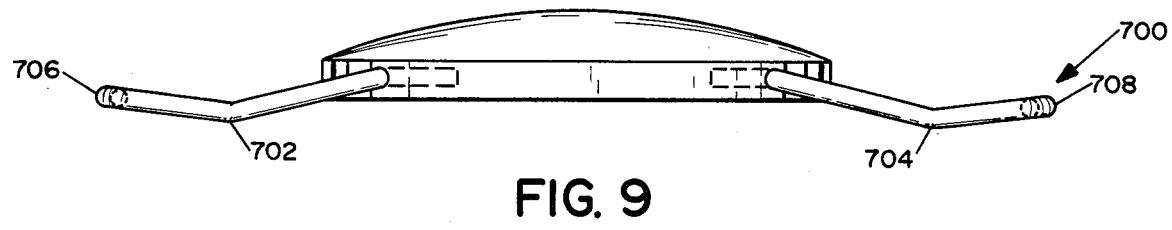
FIG. 9 illustrates a side view of the lens of FIG. 6 with a substantially kicked-up end.

FIG. 9 illustrates a side view of a lens 700 including kicked-up base ends 706 and 708 with curved ends as illustrated in FIG. 6, and apexes 702 and 704 at the junctions of the ramped portions and the kicked-up base end portion of each of the loops. This figure is similar to that of FIG. 5 and including the inward curved ends of FIG. 6.

The kicked up ends of each base of the loop can be in the range of 0.0 mm–0.25 mm while 0.12 mm appears to be the preferred value in the range at this time. The kicked up ends of the base eliminates and reduces ovaling of the pupil while also stopping the lens from bowing forward. In the event a surgeon puts in an oversized lens, the kicked up ends accomdate for the oversized lens.

PREFERRED MODE OF OPERATION—SURGICAL TECHNIQUE

The following is one insertion process for the lens 10 in an eye 74.

For pupillary dilation prior to surgery, 1% Cyclogyl and 10% Neo-Synephrine are utilized and frequently include ¼% Isoptohyoscine for extracapsular procedures to adequately maintain pupillary dilation during phacoemulsification.

The surgical procedure currently suggested and utilized includes a bridle suture through the superior rectus, and a fornix-based flap. If the horizontal corneal diameter from nine to three o'clock (measuring from the white of the limbus on one side to the white of the limbus on the other side) has not been previously calculated, the diameter should now be measured, or if previously measured, the diameter may now be re-checked.

A partial penetrating incision is now made at the limbus with a No. 57 Beaver blade. The incision should be of sufficient size to allow an intracapsular extraction with care taken with the incision site. If the incision site is too much on the corneal side of the limbus, corneal emdothelium may strip easily during surgical maneuvers, or if the incision is too far on the scleral side of the limbus, problems are encountered with the iris and bleeding is more likely if such occurs.

Two 8-0 absorbable sutures are now pre-placed at ten and two o'clock. The anterior chamber is now entered with a superblade or bladebreaker, and the incision completed with right and left curved corneal scissors with the outer blade sliding under the pre-placed sutures to avoid cutting the sutures. An 8-0 silk suture can be placed through the corneal side of the incision at twelve o'clock to be used as a traction suture by a surgical assistant to lift the cornea at the time of delivery of the cataract. This suture is later removed.

Chrymotrypsin is generally instilled under the iris to aid zonulysis after the formation of a peripheral iridectomy at twelve o'clock. The iridectomy does not need to be in the extreme periphery, and a round or oval shape is preferable. The cataract is delivered using a cryophake after the anterior chamber has been gently flushed with balanced salt solution to wash out the loose zonular material. If this has been a planned extracapsular extraction, a small central discission of the posterior capsule prior to air insertion and lens implant insertion is done thereby assuring excellent visibility for this procedure. Miochol is now instilled in the anterior chamber to constrict the pupil prior to lens implant insertion. Prior to implant insertion, air should also be inserted in the anterior chamber to prevent contact of the endothelium with the implant.

The eye is now ready for intraocular lens insertion. The size of the lens 10 to be inserted in a given eye is similar to other types of anterior chamber lenses; namely, one millimeter larger on the diagonal measurement of the implant than the horizontal diameter of the cornea at its widest point, measuring from the white of the limbus to the white on the opposite side. An 11.5 mm limbal measurement would therefore correspond to a 12.5 mm lens implant.

Ultrasonic axial length determinations and corneal keratometer readings are used to determine implant spherical power. Dioptric implant power calculations are substantially and appear to be nearly the same as for other styles of anterior chamber lenses.

Following removal of the lens 10 from a sterile package, the lens 10 should be inspected under the microscope or surgical loop prior to wetting witn balanced salt solution. The loops should be rectangular and not skewed to the right or the left. One arm of the loop should not be longer than the other. The two loops should be gently grasped with two smooth pickups and slightly wiggled to show they are intact. The diagonal diameter can also be checked at this time with a millimeter ruler or Stahl measuring device. If there is any question, the implant should be flushed with balanced salt solution and reinspected, which will almost always show the implant to be intact. The lens body and loops should be clear.

The most difficult part for the beginning implant surgeon is holding the lens. Almost any type of smooth pickup can be used with success. A small, angled, smooth pickup is favored. Lens holders for other anterior chamber lenses can also be used but those with serrated jaws should be avoided and application of too much pressure on the loop should also be avoided, as this will score the material, introducing roughness at that point and defeating one of the features of the lens. Also, extreme pressure could conceivably crack the loop although this is unlikely.

The implant lens 10 is handled like any other fine optical device, not because it is fragile, which it is not, but to avoid damaging the optical and smooth qualities of the lens. This applies to all implants. Also, touching the lens with a gloved finger or laying the implant temporarily on a surface which may contain lint can cause traces of powder or lint to be picked up by the lens and carried into the eye, causing post-operative inflammation for which the lens implant or the manufacturer would be blamed. The implant should be flushed with balanced salt solution just prior to insertion.

Insertion of anterior chamber lenses is easier with a myopic pupil. If the pupil is not small following cataract extraction, Miochol is used to constrict it. An iridectomy can be performed before or after cataract extraction and lens implantation, generally using one iridectomy inside the superior loop.

Also, if the chamber is not deep, air in the anterior chamber will make insertion of the inferior loop easier and also protect the endothelium from touching the lens. If one has difficulty maintaining the anterior chamber during insertion, the A-C is temporarily overdistended with air and the excess removed if necessary just prior to the insertion of the superior loop.

The lens 10 is held with a smooth pickup in the middle of the superior loop and the lens 10 slid in horizontally with minimal separation of the incision, thereby maintaining the air in the anterior chamber and protecting the endothelium. A traction suture through the corneal side of the incision at twelve o'clock aids in this maneuver. Slight traction on this suture will slightly separate the lips of the incision and the lens can be slid in without losing camber.

Once the inferior loop is past the inferior pupillary border, the grip on the superior loop with the smooth pickup can be released completely and the implant advanced into the anterior chamber by tap ing the superior loop gently with the edge of the smooth pickup. At this point, if there is too much air in the anterior chamber, the inferior loop will rest on the iris below the inferior angle recess. Because of the lightness of the lens 10, removing excess air with a 30-gauge cannula at this point will cause the inferior loop and iris to rise. This should be done until the inferior loop is level with the inferior angle recess. This is an important procedural point, and following this procedure will insure that the inferior loop will not be inserted posteriorly to the angle recess when the superior loop is inserted.

The iris at this point sometimes seems to stick to the under surface of the lens, and grasping the superior loop with two smooth pickups (one in each hand) and rocking the inferior loop back and forth several times like the pendulum of a clock will break the iris free and insure that the iris is not carried into the angle recess or tucked.

Because of the slight flexibility of the loops, the entire superior loop can be inserted in one motion. This also avoids dislocating a portion of the inferior loop. The scleral side of the incision is grasped with a toothed pickup and the superior loop in the middle with a smooth pickup. Pulling the sclera towards one's self, with one motion the surgeon pushes the entire loop slightly inferiorly and then posteriorly into the angle recess, always pulling the scleral side or the wound toward one's self rather than shoving the lens inferiorly too vigorously as this can cause an angle tear and recession just as with other anterior chamber style lenses. This is an important point.

At this stage with the anterior chamber adequately formed, the pupil should be central and round. If the pupil is oval superior-inferiorly, it may mean the implant is too large. If the pupil is irregular, it may point to an iris tuck which usually does not occur with the lens 10. The lens 10 can easily be repositioned at this point. Irregular pupils may however be due to the use of dilating drops, paresis of the sphincter from stretching the iris in removing a cataract through a small pupil, or localized blood in the anterior chamber. The corneal side of the incision should be lifted slightly to inspect the superior loop to make sure the entire loop has been inserted past the scleral edge of the incision and is in the angle recess.

The implant should be snug but not too tight. Using a 30-gauge cannula and nudging the superior loop sideways, it should move easily but not be loose. This maneuver can also be used to position the lens centrally, with the great majority of implants used 12.5 mm. in size. If a choice is to be made, the surgeon should lean toward a less snug fit than one too tight. Also, the limbal measurement does not always conform to the formula given for the size of the implant. Again, the transition zone at the limbus may be indistinct or wider than usual, and these variations should be taken into account and allowances made at the time of surgery.

At this point, the peripheral iridectomy should be between the two vertical arms of the superior loop. The 8-0 absorbable sutures are now tied. The wound is further closed with crossing "X" type mattress sutures using 10-0 Nylon and additional 8-0 absorbable interrupted sutures. However, a closure should be done which is comfortable for the surgeon and results in a snug wound. A tighter closure will result in munus cylinder at 180°, which is much more desirable than minus cylinder at 90°, indicating a too-loose closure. In addition, minus cylinder at 180° tends to decrease with time, and the Nylon sutures may be cut to aid in this process. Minus cylinder at 90° tends to increase for a period of time following surgery, which is also undesirable. The depth of the sutures also appears to affect the changes in cylinder. Deeply placed sutures may allow no change in cylinder from that noted in the first several post-operative visits, while conversely, shallow suture placement will allow a gradual shift of astigmatic minus cylinder from 180° toward 90° for a period of time following surgery. Ideally, of course, no astigmatic cylinder at all is the goal. At present, it is preferable to conclude with about $-2.00$ diopters of cylinder at 180° at the conclusion of surgery.

Miochol is now used to deepen the anterior chamber and further constrict the pupil. The conjunctival flap is secured at the limbus with thermal cautery. A ½ cc. of Celestone may be placed subconjunctively in the inferior cul-de-sac to reduce inflammatory reaction. Neosporin ophthalmic drops are generally flushed about the globe prior to the start of surgery, and again at the conclusion of surgery. A patch and shield are placed until the day following surgery. A shield only is worn at night during sleep for about three weeks. Post-operative medication consists of Maxitrol drops, one/two drops three times daily. Later, Steroid drops only may be used if post-operative inflammation persists.

Older patients are generally discharged from the hospital on the second post-operative day, but discharge the day following surgery is not unusual. An operative procedure at a surgi-center with discharge home or to an extended care facility may also be generally acceptable. No restriction is placed on general activities, but vigorous activity and heavy lifting should be avoided for a period of time following surgery.

Extracapsular cases are done using either the Kelman Phacoemulsification Unit or by simple expression and removal of the cortex by hand-operated irrigating and suction tips.

The lens is manufactured by known processes and can be a multiplicity of cylindrical loops or ribbons produced concurrently or assembled for the loops or like structures of predetermined geometrical configurations in lieu of the loops. Opotic and loop structure can be manufactured from a single piece of material such as PMMA or the like.

Various modifications can be made to the present invention without departing from the apparent scope thereof. Other two- or multi-structure configurations are within the scope of the invention, especially two-loop configurations. Other geometrical configurations are within the scope and teachings of this patent, especially where the lens is composed of a second material while the loops are composed of PMMA.

The lens can take other geomerrical configurations such as aspheric, convex-convex, or convex-concave, and the disclosure is not solely limited to the plano-convex configuration. The lens could be made of material other than PMMA.

Finally, while the flexible loops are illustrated as closed loops, other loop structures are within the teachings and scope of the present invention. The two flexible loops can be a continuous single loop or can be more than two loops.

Each of the loops can be a single monofilament strand of PMMA having one end attached to the optic and assuming a predetermined geometrical shape such as an open loop having one free end, a "W" configuration, a "J" configuration, an "S" configuration, or any other predetermined geometrical configuration in lieu of the closed loop U-shaped configuration as illustrated.

The loops, also disclosed as strands and ribbons, can be produced simultaneoulsy with the lens of assembled individually to the lens.

While the loops have been illustrated in a closed configuration, the end of the loop could be open or, in the alternative, the base of the loop could be open with the arms of the loops being either straight or in a preformed geometrical configuration.

It is important that whatever configuration the loops take, the loops can be provided with a ramp to vault the lens away from the iris as desired.

The principle of the kicked up end is applicable to open end loops and closed end loops. The principle can be applied to any style of lens-either anterior or posterior chamber lens. The principle is also applicable to any style of feet, bases, or loops.

Having thus described the invention, what is claimed is:

1. Anterior chamber lens comprising:
   a. lens optic;
   b. two opposing ramped U-shaped loops, each of said loops formed of a smooth, round, cylindrical member, and each of said loops including substantially rounded corners, each of said loops secured into opposing sides of said lens optic; and,
   c. each of said loops including a kicked-up end means including an end portion of each of said loops angled upwardly a finite height whereby said loops provide three-dimensional stability and flexibility in both primary and secondary implantations with either intracapsular or extracapsular cataract extractions and said kicked-up end means prevents ovaling of a pupil of an eye and bowing of said lens forward in said eye.

2. Lens of claim 1 wherein said kicked-up end provides a slightly planar portion to each of said loops between said kicked-up end means and said ramped loops.

3. Lens of claim 1 wherein said kicked-up end means provides an apexed portion between said ramped loops and said kicked-up end means.

4. Lens of claim 1 wherein ends of said loops are curved inwards.

5. Lens of claim 1 wherein said kicked-up end means are in a range of 0.05–0.25 mm from a lowest point of each of said loops.

6. Lens of claim 1 wherein said kicked-up end means are at 0.12 mm from a lowest point of each of said loops.

* * * * *